United States Patent
Yu

(10) Patent No.: US 8,216,196 B2
(45) Date of Patent: Jul. 10, 2012

(54) WOUND TREATMENT APPARATUS AND GUIDING UNIT THEREOF

(75) Inventor: Tung-Ming Yu, Yilan County (TW)

(73) Assignee: Industrial Technology Research Institute, Hsinchu (TW)

( * ) Notice: Subject to any disclaimer, the term of this patent is extended or adjusted under 35 U.S.C. 154(b) by 501 days.

(21) Appl. No.: 12/491,131

(22) Filed: Jun. 24, 2009

(65) Prior Publication Data

US 2010/0168687 A1 Jul. 1, 2010

(30) Foreign Application Priority Data

Dec. 31, 2008 (TW) .............................. 97151796 A

(51) Int. Cl.
*A61M 1/00* (2006.01)
(52) U.S. Cl. ........................................ 604/313; 604/319
(58) Field of Classification Search ............ 604/164.01, 604/304, 305, 307, 313, 317, 319; 602/41, 602/43; 4/541.1
See application file for complete search history.

(56) References Cited

U.S. PATENT DOCUMENTS

| | | | | |
|---|---|---|---|---|
| 5,141,498 | A | * | 8/1992 | Christian ................. 604/167.03 |
| 6,142,982 | A | | 11/2000 | Hunt et al. |
| 6,224,561 | B1 | * | 5/2001 | Swendson et al. ............ 600/562 |
| 6,648,862 | B2 | | 11/2003 | Watson |
| 2005/0020955 | A1 | | 1/2005 | Sanders et al. |
| 2007/0219512 | A1 | * | 9/2007 | Heaton et al. ................. 604/304 |

* cited by examiner

*Primary Examiner* — Melanie Hand

(57) ABSTRACT

A wound treatment includes a guiding unit and a negative pressure collecting module. The guiding unit includes a main body, an elastic member and an accommodating portion formed within the elastic member. The main body has a first end is communicated to the wound, and a second end. The elastic member is disposed in the main body to isolate the first end from the second end. The negative pressure collecting module, connecting with the guiding unit, includes a negative pressure source providing negative pressure to the wound, and a collecting device collecting exudates of the wound. When the negative pressure source sucks air from the guiding unit, the elastic member deforms, and the accommodating portion communicates with the first end and the second end, respectively. When the negative pressure source stops sucking, the elastic member is restored, and the accommodating portion isolates the first end from the second end.

16 Claims, 8 Drawing Sheets

WOUND TREATMENT APPARATUS AND GUIDING UNIT THEREOF

CROSS REFERENCE TO RELATED APPLICATIONS

This Application claims priority of Taiwan Patent Application No. 097151796, filed on, Dec. 31, 2008, the entirety of which is incorporated by reference herein.

BACKGROUND OF THE INVENTION

1. Field of the Invention

The present invention relates to a wound treatment apparatus and a guiding unit thereof, and in particular, to a wound treatment apparatus collecting exudates from a wound and to a guiding unit preventing the exudates from flowing backward.

2. Description of the Related Art

Negative pressure wound therapy utilizes a vacuum pump combined with wound dressing, a flexible sucker disk and biocompatible porous material to provide a negative pressure atmosphere around the wound. The exudes and infected tissues are sucked out, and healthy tissue fluid, is extracted to maintain a moist therapeutic environment around the wound to improve blood microcirculation and to promote or assist in healing of the wound.

U.S. Pat. No. 6,648,862 discloses a personal and portable vacuum desiccator provided with a one-way valve disposed proximate to an inlet port of the desiccator cartridge to prevent the contents of the desiccator cartridge from flowing backward out of the inlet port. However, the personal and portable vacuum desiccator cannot prevent gas/liquid remaining in the pathway from flowing backward to the wound. In other words, when the vacuum device stops operation, gas/liquid on the way to the desiccator cartridge flows back to the wound to promote infections.

BRIEF SUMMARY OF THE INVENTION

Accordingly, the invention provides a wound treatment apparatus. The wound treatment apparatus comprises a guiding unit and a negative pressure collecting module. The guiding unit comprises a main body, an elastic member and an accommodating portion. The main body has a first end and a second end, wherein the first end is communicated to the wound. The elastic member is disposed in the main body to isolate the first end from the second end. The accommodating portion is formed within the elastic member. The negative pressure collecting module, connecting with the guiding unit, comprises a negative pressure source and a collecting device. The negative pressure source provides negative pressure to the wound, and the collecting device collects exudates of the wound. When the negative pressure source sucks air (e.g. providing negative pressure) from the guiding unit, the elastic member deforms, and the accommodating portion communicates with the first end and the second end, respectively. When the negative pressure source stops the sucking action (e.g. the negative pressure source stop operation), the elastic member is restored, and the accommodating portion isolates the first end from the second end.

The invention provides a guiding unit connecting to a negative pressure source. The guiding unit comprises a main body, an elastic member and an accommodating portion. The main body has a first end and a second end, wherein the first end is communicated to the wound. The elastic member is disposed in the main body to isolate the first end from the second end. The accommodating portion is formed within the elastic member. When the negative pressure source sucks air (e.g. providing negative pressure) from the guiding unit, the elastic member deforms, and the accommodating portion communicates with the first end and the second end, respectively. When the negative pressure source stops the sucking action (e.g. the negative pressure source stop operation), the elastic member is restored, and the accommodating portion isolates the first end from the second end.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

Figure 1:
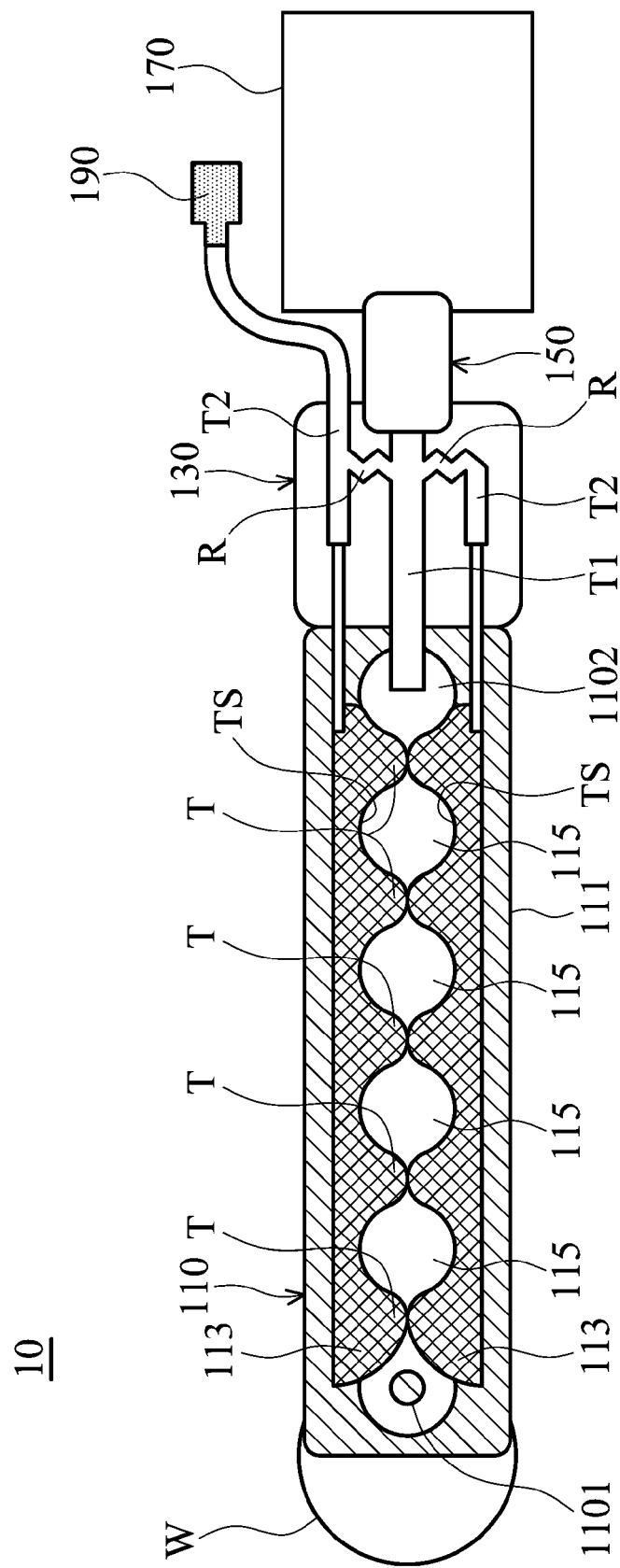
FIG. 1 is a schematic view of an embodiment of a wound treatment apparatus of the invention.
Figure 2:
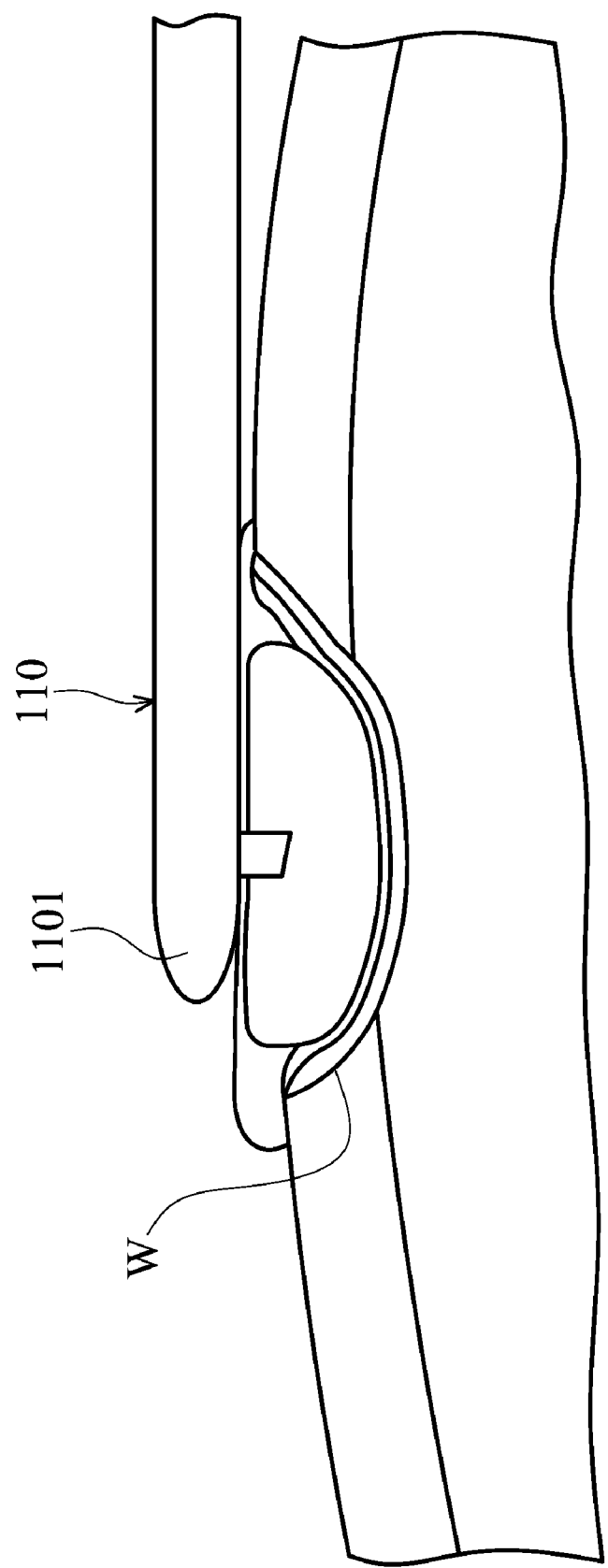
FIG. 2 is a schematic view showing the wound treatment apparatus of FIG. 1 connecting to a wound.
Figure 3A:
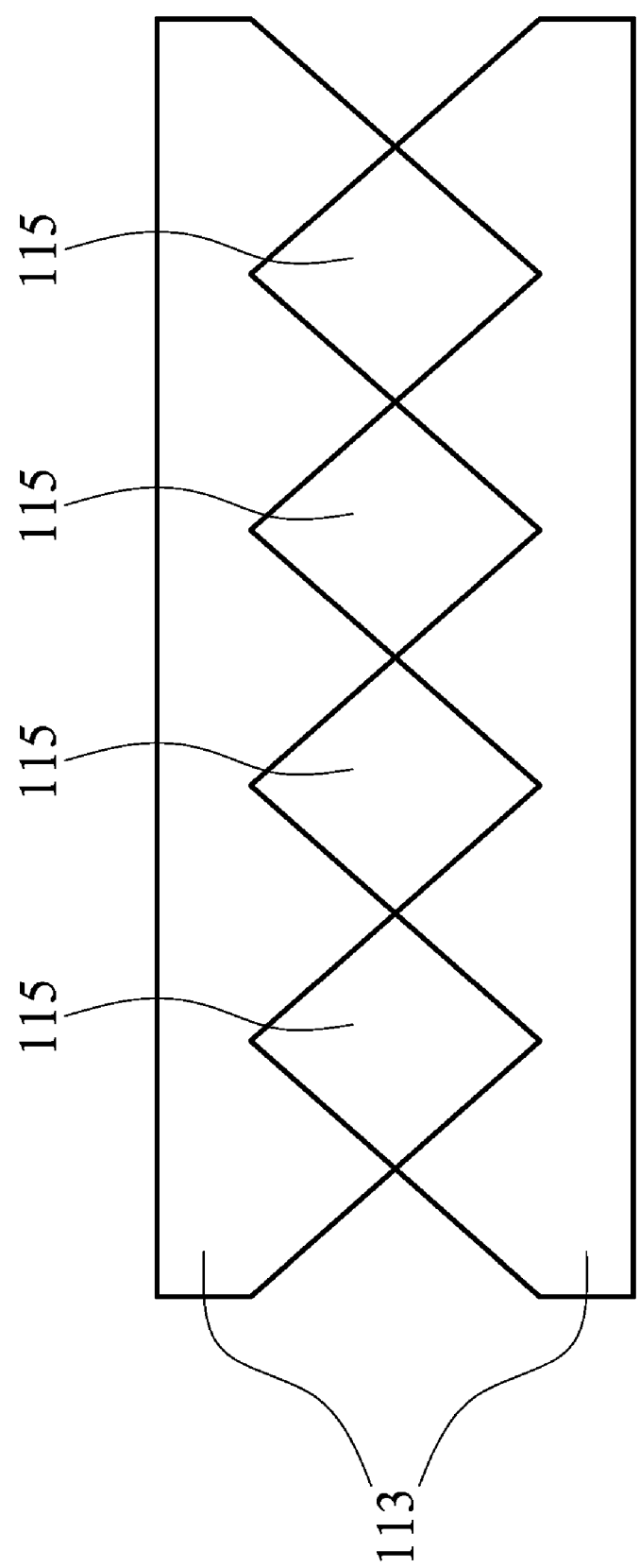
FIG. 3A is a schematic view of an embodiment of an elastic member of the wound treatment apparatus of the invention.
Figure 3B:
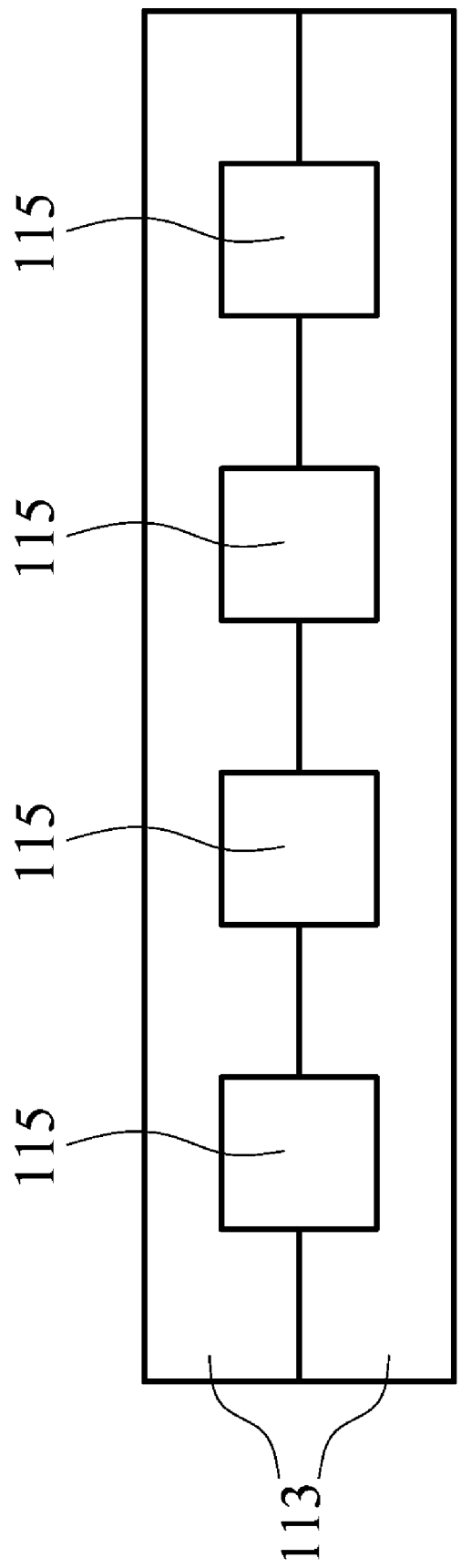
FIG. 3B is a schematic view of another embodiment of an elastic member of the wound treatment apparatus of the invention.

FIG. 1 is a schematic view of an embodiment of a wound treatment apparatus of the invention. FIG. 2 is a schematic view showing the wound treatment apparatus of FIG. 1 connecting to a wound. FIG. 3A is a schematic view of an embodiment of an elastic member of the wound treatment apparatus of the invention. FIG. 3B is a schematic view of another embodiment of an elastic member of the wound treatment apparatus of the invention. Referring to FIGS. 1 and 2, the wound treatment apparatus 10 connects to the wound W (as shown in FIG. 2) to guide out exudates F produced by the wound W. The wound treatment apparatus 10 comprises a guiding unit 110 and a negative pressure collecting module. Specifically, the wound treatment apparatus 10 comprises a guiding unit 110, a connecting unit 130, a negative pressure source 150, a collecting device 170 and a pressure sensor 190.

In the embodiment, the guiding unit 10 comprises a main body 111, two elastic members 113 and four accommodating portions 115. The main body 111 has a first end 1101 and a second end 1102. The first end 1101 connects to the wound W, and an airtight space is formed at the first end 1101 with aid of a wound dressing, a flexible sucker disk and a biocompatible porous material (as shown in FIG. 2). The second end 1102 communicates with the negative pressure collecting module via the connecting unit 130.

Each of the elastic members 113 is porous elastic material or elastic polymer and comprises an impermeable exterior surface TS covering the porous elastic mater or elastic polymer. The two elastic members 113 are disposed in the main body 111 to isolate the first end 1101 from the second end

1102. Each elastic member 113 comprises five teeth T, and every accommodating portion 115 is formed within the elastic members 113, between two adjacent teeth T. By abutting the teeth T of the two elastic members 113, the accommodating portions 115 are isolated from each other, and the first end 1101 is isolated from the second end 1102, simultaneously.

Referring to FIGS. 3A and 3B, it should be noted that the embodiment comprises two elastic members 113, but it is not limited thereto. The number of elastic members 113 is selected to be one or plural according to requirement. Furthermore, the teeth T of the elastic member 113 are curved in the embodiment, but the teeth T can also be triangular (as shown in FIG. 3A), rectangular (as shown in FIG. 3B) or other shapes. The number of the teeth T is not limited, as long as at least one accommodating portion 115 can be formed therebetween. Preferably, the number of the teeth T is more than two.

Referring to FIG. 1 again, the connecting unit 130, connecting to the guiding unit 110 and the negative pressure collecting module, comprises a first conduit T1 and two second conduits T2. The first conduit T1 communicates with the second end 1102 of the guiding unit 110 with the negative pressure collecting module. The two second conduits T2 respectively communicate the two elastic members 113 with the first conduit T1. At the connections between the first conduit T1 and the two second conduits T2, flow-resist structures R are formed by bending of the conduits. The pressure sensor 190 is connected to any of the second conduits T2.

It should be noted that the connecting unit 130 comprises two second conduits T2 to respectively communicate with the two elastic members 113 in the embodiment, which means the number of the second conduits T2 is selected to match the number of the elastic members 113. When the elastic members 113 are multiple, the second conduits T2 are correspondingly multiple.

The negative pressure collecting module, communicated to the guiding unit 110, comprises the negative pressure source 150 and the collecting device 170, wherein the negative pressure source 150 supplies negative pressure and the collecting device 170 collects exudates F from the wound W. In the embodiment, the negative pressure source 150 is disposed between the connecting unit 130 and the collecting device 170. Specifically, the negative pressure source 150 is disposed on the first conduit T1, and connects with the guiding unit 110 via the connecting unit 130. The negative pressure source 150 sucks air out of the guiding unit 110 (negative pressure source 150 provides negative pressure) to form a negative pressure environment around the wound W, and simultaneously the exudates F is delivered to the collecting device 170 to maintain cleanliness of the wound W. In another embodiment, the negative pressure collecting module communicates with the guiding unit 110 via the collecting device 170. That is, the collecting device 170 is disposed between the connecting unit 130 and the negative pressure source 150. Specifically, the collecting device 170 is disposed on the first conduit T1 and connects with the guiding unit 110 via the connecting unit 130.

Figure 4A:
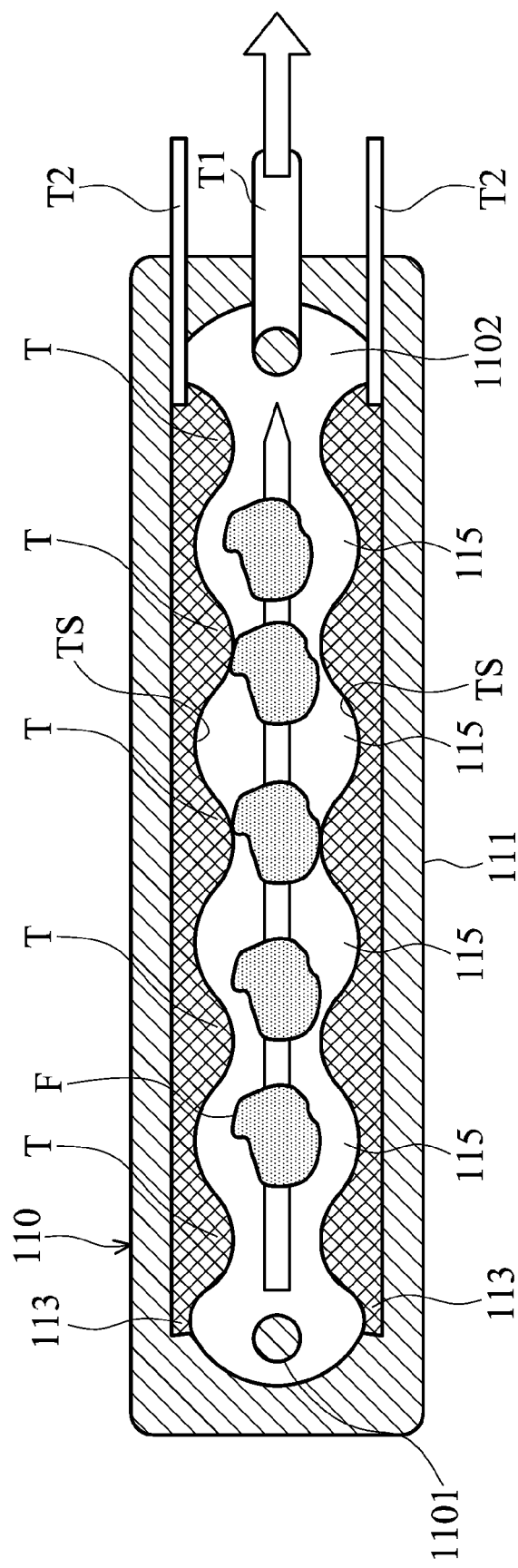
FIG. 4A is a schematic view of an embodiment of a deformed elastic member according to the wound treatment apparatus of the invention.

FIG. 4A is a schematic view of an embodiment of a deformed elastic member according to the wound treatment apparatus of the invention. Referring to FIG. 1 and FIG. 4 at the same time, to operate the wound treatment apparatus 10, the negative pressure source 150 is turned on to suck air out of the guiding unit 110. Meanwhile, the negative pressure source 150 sucks air from the elastic members 113 via the second conduits T2. Air in the pores of the elastic members 113 is sucked out and the elastic members 113 are compressed to deform. The deformation of the elastic members 113 allows the accommodating portions 115 to communicate with each other, and further communicate the first end 1101 with the second end 1102, such that the negative pressure source 150 is able to suck exudates F from the first end 1101 to the second end 1102, and collect the exudates F in the collecting device 170 (as shown by the arrow in FIG. 4A).

Figure 4B:
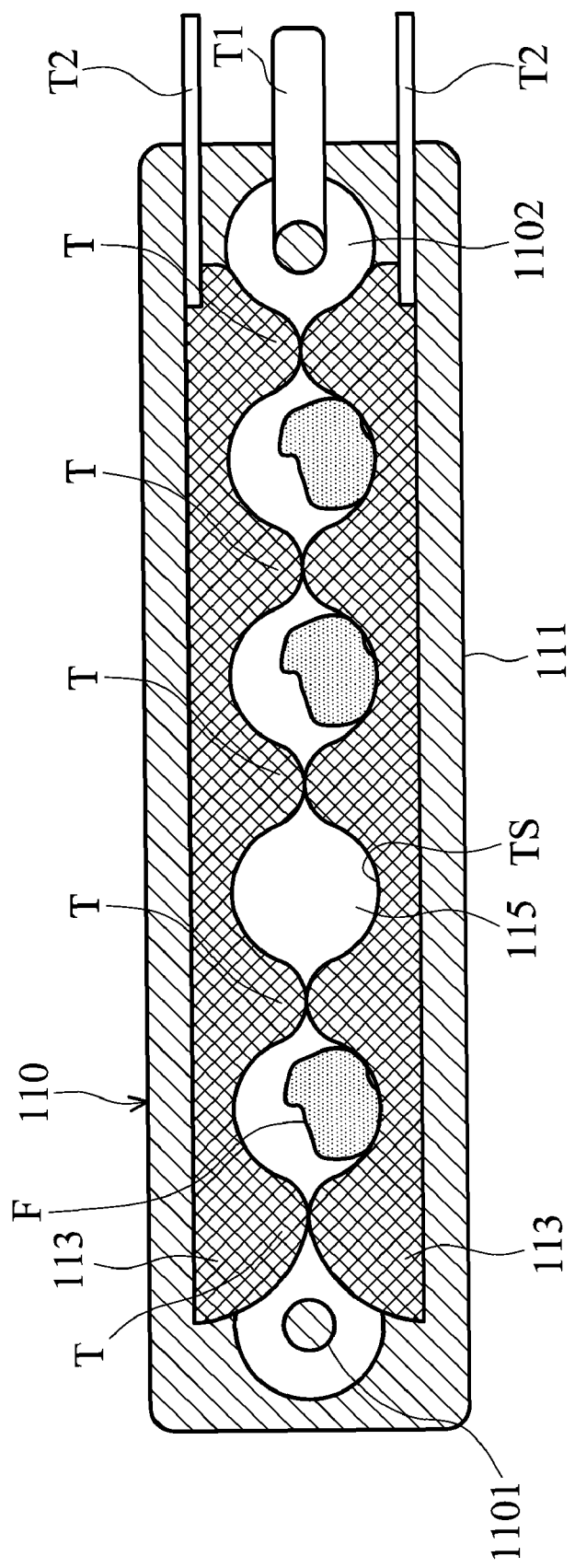
FIG. 4B is a schematic view of an embodiment of a restored elastic member according to the wound treatment apparatus of the invention.

FIG. 4B is a schematic view of an embodiment of a restored elastic member according to the wound treatment apparatus of the invention. Referring to FIG. 4B, when the negative pressure source 150 stop operating (the negative pressure source 150 exhausts air), the elastic members 113 restore to their original shapes, such that the accommodating portions 115 are isolated from each other again, and the first end 1101 and the second end 1102 are isolated. Meanwhile, exudates F are clamped by the elastic members 113 and maintained in the accommodating portions 115. In other words, exudates F are kept in the accommodating portions 115, and do not flow backward to the first end 1101 to contact the wound W, therefore avoiding infections.

Figure 5A:
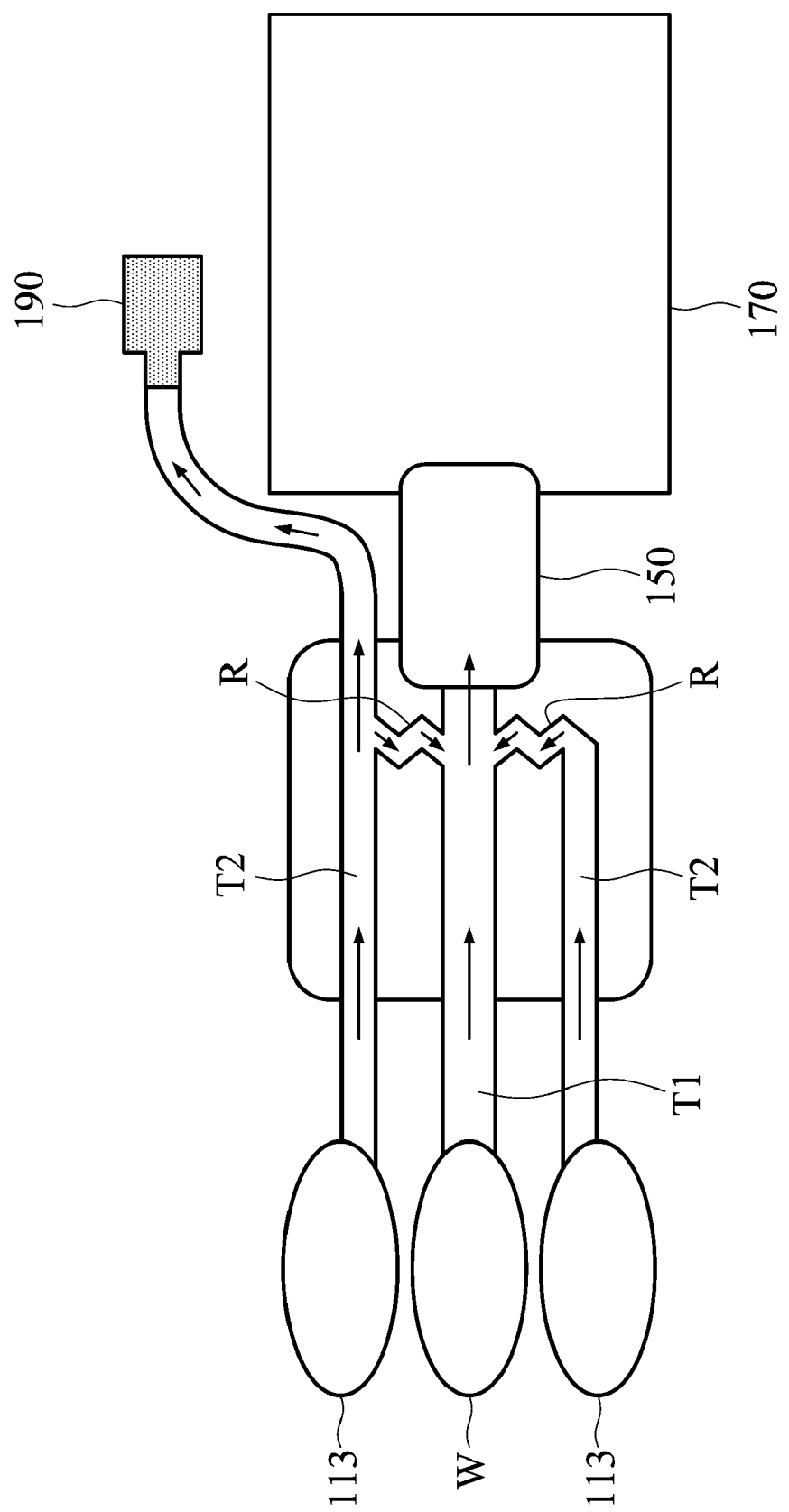
FIG. 5A is a schematic view of an embodiment showing airflow in a connecting unit of the invention.
Figure 5B:
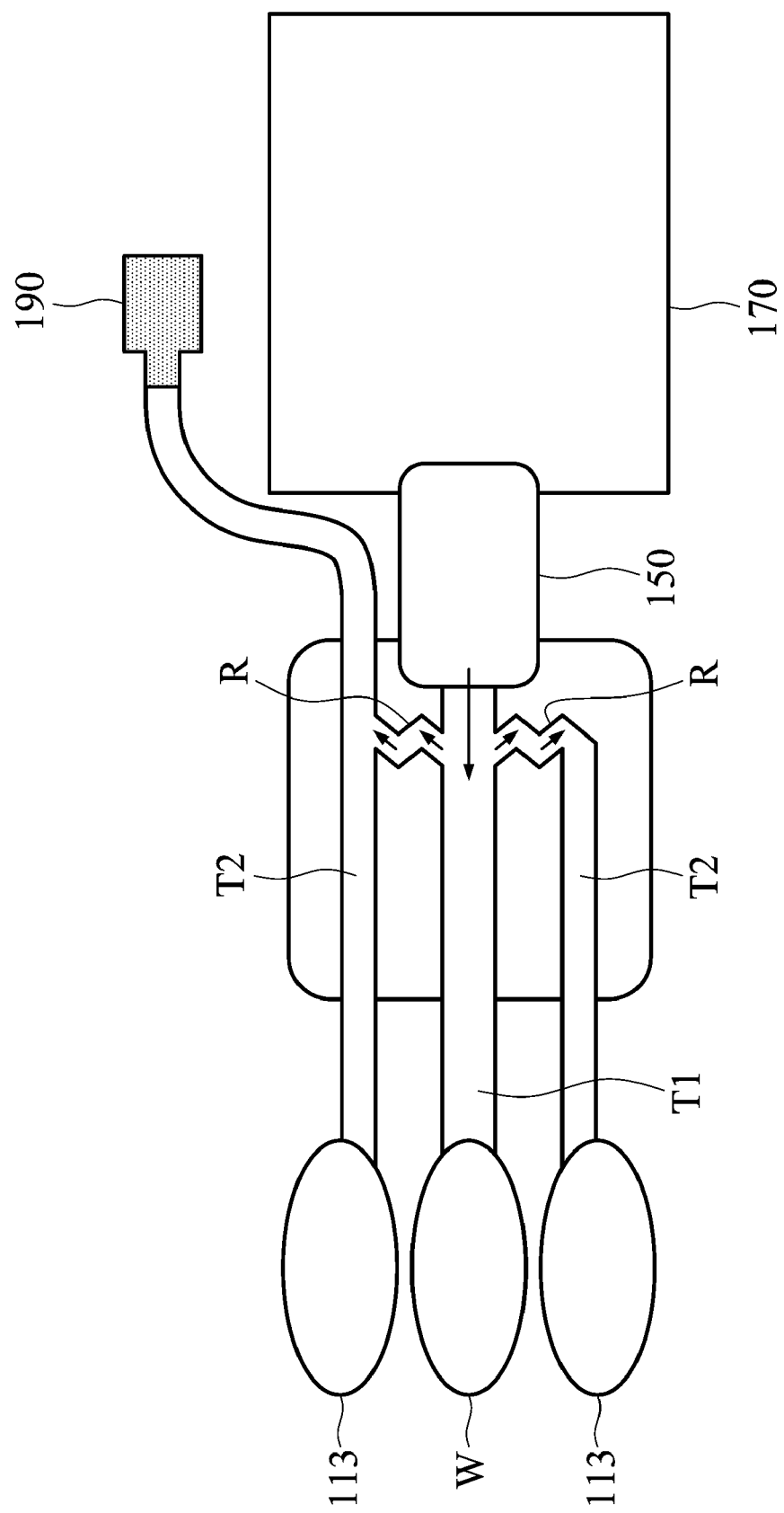
FIG. 5B is a schematic view of an embodiment showing airflow in a connecting unit of the invention.

FIGS. 5A and 5B are schematic views of an embodiment showing airflow in a connecting unit of the invention. Referring to FIG. 5A, because the first conduit T1 communicates with the second conduits T2, the pressures in all the conduits are the same. When the negative pressure source 150 starts the sucking action (airflow as shown by the arrow in FIG. 5A), the pressure sensor 190 connected with the second conduits T2 directly detects the pressure at the wound site by communication between the first conduit T and the second conduits T2. Referring to FIG. 5B, when the negative pressure source 150 stop the sucking action (airflow as shown by the arrow in FIG. 5B), air in the first conduit T1 and the second conduits T2 slightly flows backward, but exudates F in the first conduit T1, blocked by the flow-resist structures R, do not flow into the second conduits T2. Therefore, the elastic members 113 and the pressure sensor 190 connected with the second conduits T2 do not contact the exudates F.

The elastic members 113 of the guiding unit 110 in the wound treatment apparatus 10 of the invention successfully prevents exudates F from flowing backward to the wound W during exhaustion of the negative pressure source 150 to avoid infections. Moreover, the flow-resist structures R of the connecting unit 130 in the wound treatment apparatus 10 of the invention decreases damage to the pressure sensor 190 by eliminating contact between the exudates F and the pressure sensor 190.

While the present invention has been described by way of example and in terms of the embodiment, it is to be understood that the present invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A wound treatment apparatus applied to a wound, comprising
   a guiding unit, comprising:
      a main body having a first end and a second end, wherein the first end is communicated to the wound;
      an elastic member, disposed in the main body to isolate the first end from the second end, the elastic member comprising a plurality of teeth;
      an accommodating portion formed within the elastic member between two adjacent teeth;
   a negative pressure collecting module connecting with the guiding unit, comprising:
      a negative pressure source providing negative pressure to the wound; and a collecting device collecting exudates of the wound;

wherein when the negative pressure source sucks air from the guiding unit, the elastic member deforms to allow the accommodating portion to communicate with the first end and the second end, respectively, and when the negative pressure source stops the sucking action, the elastic member is restored to allow the accommodating portion to isolate the first end from the second end.

2. The wound treatment apparatus as claimed in claim 1, wherein the number of the accommodating portion is plural, and when the negative pressure starts the sucking action, the elastic member deforms to allow the accommodating portions to communicate with each other.

3. The wound treatment apparatus as claimed in claim 1, wherein the elastic member is of porous elastic material or elastic polymer and comprises an impermeable exterior surface.

4. The wound treatment apparatus as claimed in claim 1, further comprising a connecting unit connecting the guiding unit and the negative pressure collecting module together, wherein the guiding unit communicates with the negative pressure collecting module via the connecting unit.

5. The wound treatment apparatus as claimed in claim 4, wherein the connecting unit comprises:
   a first conduit communicating with the main body and the negative pressure collecting module; and
   a second conduit communicating with the elastic member and the first conduit.

6. The wound treatment apparatus as claimed in claim 5, wherein the connecting unit further comprises a flow-resist structure disposed between the first conduit and the second conduit.

7. The wound treatment apparatus as claimed in claim 5, further comprising a pressure sensor connected with the second conduit.

8. The wound treatment apparatus as claimed in claim 5, wherein the negative pressure source is disposed on the first conduit, and the negative pressure source is connected with the guiding unit via the first conduit.

9. The wound treatment apparatus as claimed in claim 5, wherein the collecting device is disposed on the first conduit, and the collecting device is connected with the guiding unit via the first conduit.

10. The wound treatment apparatus as claimed in claim 1, wherein the number of the elastic member is two, and the accommodating portion is formed between the two elastic members.

11. The wound treatment apparatus as claimed in claim 1, wherein the teeth are curved, rectangular or triangular.

12. A guiding unit connecting to a negative pressure source, comprising
   a main body having a first end and a second end, wherein the first end is communicated to the wound;
   an elastic member, disposed in the main body to isolate the first end from the second end, the elastic member comprising a plurality of teeth; and
   an accommodating portion formed within the elastic member between two adjacent teeth,
   wherein when the negative pressure source sucks air from the guiding unit, the elastic member deforms to allow the accommodating portion to communicate with the first end and the second end, respectively, and when the negative pressure source stops the sucking action, the elastic member is restored to allow the accommodating portion to isolate the first end from the second end.

13. The guiding unit as claimed in claim 12, wherein the number of the accommodating portion is plural, and when the negative pressure starts the sucking action, the elastic member deforms to allow the accommodating portions to communicate with each other.

14. The guiding unit as claimed in claim 12, wherein the elastic member is of porous elastic material or elastic polymer and comprises an impermeable exterior surface.

15. The guiding unit as claimed in claim 12, wherein the number of the elastic member is two, and the accommodating portion is formed between the two elastic members.

16. The guiding unit as claimed in claim 12, wherein the teeth are curved, rectangular or triangular.

* * * * *